United States Patent [19]

Jones

[11] Patent Number: 5,716,991
[45] Date of Patent: Feb. 10, 1998

[54] PHARMACEUTICAL COMPOSITIONS COMPRISING PARACETAMOL AND L-CYSTEINE OR A PRECURSOR THEREOF

[75] Inventor: Roger Spencer Jones, Powys, Wales

[73] Assignee: British Technology Group Limited, London, England

[21] Appl. No.: 513,990

[22] PCT Filed: Mar. 8, 1994

[86] PCT No.: PCT/GB94/00446

§ 371 Date: Sep. 5, 1995

§ 102(e) Date: Sep. 5, 1995

[87] PCT Pub. No.: WO94/20086

PCT Pub. Date: Sep. 15, 1994

[30] Foreign Application Priority Data

Mar. 12, 1993 [GB] United Kingdom ............... 9305058.1

[51] Int. Cl.$^6$ .................. A61K 31/05; A61K 31/95; A61K 31/16; A61K 31/35
[52] U.S. Cl. .................. 514/562; 514/630; 514/823; 514/710; 514/922; 424/10
[58] Field of Search .................. 514/562, 630, 514/823, 625, 710, 922; 424/10

[56] References Cited

FOREIGN PATENT DOCUMENTS

| 0 040 472 | 11/1981 | European Pat. Off. . |
| 0 100 168 | 2/1984 | European Pat. Off. . |
| 0 130 683 | 1/1985 | European Pat. Off. . |
| 1 003 065 | 9/1965 | United Kingdom . |
| 1 287 431 | 8/1972 | United Kingdom . |
| 1 463 505 | 2/1977 | United Kingdom . |
| 2 124 078 | 5/1984 | United Kingdom . |

*Primary Examiner*—Keith MacMillan
*Attorney, Agent, or Firm*—Nixon & Vanderhye

[57] ABSTRACT

An improved process for the production of a pharmaceutical composition comprising p-hydroxyacetanilide and L-cysteine or a compound which is converted thereto in vivo comprises mixing p-hydroxyacetanilide and L-cysteine or its precursor in the solid state and then shaping the solid mixture.

7 Claims, No Drawings

PHARMACEUTICAL COMPOSITIONS COMPRISING PARACETAMOL AND L-CYSTEINE OR A PRECURSOR THEREOF

This application is a 371 of PCT/GB94/00446, filed Mar. 8, 1994, which claims priority to UK 9305058.1, filed Mar. 12, 1993.

This invention relates to analgesics and in particular to novel formulations of p-hydroxyacetanilide.

p-Hydroxyacetanilide or paracetamol finds wide use as an analgesic and has the particular advantage of having a relatively pure analgesic action with few side effects when used in normal dosages. However, overdoses of the drug can be very toxic and the ready availability of the drug has led to its use on a quite significant scale as a means of attempting suicide. Even when the overdose is not fatal it can lead to severe liver injury and the methods at present available for the treatment of an overdose of the drug are often ineffective in preventing this.

This problem has been recognised for a considerable time and in 1973, UK Patent Application 54098/73 was filed (published as UK Patent 1,463,505) describing a means of overcoming the problem. Thus, the toxicity of p-hydroxyacetanilide is due to the hepatic necrosis induced by a toxic metabolite to which the drug is converted in vivo. However, the compound glutathione, which is a tripeptide containing a central L-cysteine unit, is in some way involved with the toxic action of the metabolite in the body so that only when the liver has been depleted of glutathione does significant hepatic necrosis occur. Formulation of p-hydroxyacetanilide together with L-cysteine or a compound which is converted thereto in vivo has the very great advantage that an overdose of the drug automatically results in an increase in the amount of glutathione synthesised by the body thus countering the toxic effect of the overdose. The glutathione precursor may also detoxify the p-hydroxyacetanilide by providing intracellular sulphate, the formation of its sulphate being an alternative safe metabolic pathway for the disposal of p-hydroxyacetanilide.

However, although a product (Pameton) has for some time been available in the United Kingdom which avoids the dangers of overdose through the inclusion together with p-hydroxyacetanilide of the L-cysteine precursor DL-methionine, the major part of the market for p-hydroxyacetanilide is still met by products which provide no protection against an overdose. This is in significant measure due to the characteristic sulphur type odour which is associated with the marketed product that provides protection against an overdose, as discussed in UK Patent 1,583,602. It has now been found that it is possible to solve the problem of the potential extreme toxicity of overdoses of p-hydroxyacetanilide through formulating this compound together with DL-methionine or like compound in a manner which does not produce a product with a marked sulphur type odour, thereby providing a much more acceptable product which is suitable for the general market.

According to the present invention a process for the production of a pharmaceutical composition comprising p-hydroxyacetanilide and L-cysteine or a compound which is converted thereto in vivo comprises mixing p-hydroxyacetanilide and L-cysteine or its precursor in the solid state and then converting the solid mixture to a shaped product.

The term "shaped" is used herein in its normal sense of having a defined form as, for example, in a tablet, and "shaping" is used to indicate the production of such a defined form.

The problems of producing a shaped or formed product comprising p-hydroxyacetanilide are discussed in UK Patent 1,390,032 where it is indicated that a granular material must be employed for this purpose. Further attention is paid in UK Patent 2,124,078 and its equivalent European Patent Application A-0 100 168 to the problem of producing a shaped composition of p-hydroxyacetanilide, including one containing methionine, and the use of a wet-granulation technique is proposed. The final composition obtained by such techniques may not necessarily contain a significant amount of water but the defect of these prior art processes is that their initial stages involve a wet process, the production of the marketed product Pameton also involving such a process. Without limitation to any particular mode of operation, it is believed that one advantage of the present invention over the prior art lies in the avoidance of hydrolysis of the L-cysteine or its precursor with the formation of volatile sulphur-containing products.

Thus, it has now been found that it is possible to produce a solid pharmaceutical composition comprising p-hydroxyacetanilide and DL-methionine or like compound through shaping a solid mixture which is produced through admixture of the components in the solid state and that the composition, although not odourless, has a more acceptable odour than that of a composition derived from a granular product obtained by a wet process. In addition to this primary advantage the product produced by the dry process of the present invention has the further advantage of containing a high amount of p-hydroxyacetanilide per unit volume so that the size of a tablet containing a unit dosage of 500 mg p-hydroxyacetanilide is readily acceptable to the patient. The finding that p-hydroxyacetanilide and L-cysteine or a compound which is converted thereto in vivo can be directly formulated, particularly by direct compression, into a shaped pharmaceutical composition is all the more surprising in the light of the conventional view, as expressed in UK Patent 1,390,032, that the formulation of p-hydroxytacetanilide requires a granulation step.

In one aspect the present invention thus includes a solid mixture suitable for use in the manufacture of a shaped pharmaceutical product comprising p-hydroxyacetanilide and L-cysteine or a compound which is converted thereto in vivo characterised in that the mixture is of non-granular form.

In a further aspect the present invention includes a solid mixture comprising p-hydroxyacetanilide and L-cysteine or a compound which is converted thereto in vivo characterised in that the L-cysteine or its precursor is substantially of a particle size less than 1,000 microns.

Thus, it has been found that of the two major components, it is the physical form of L-cysteine or its precursor rather than that of the p-hydroxyacetanilide which is most relevant to an improvement of the prior art procedures for the formulation of the pharmaceutical composition. In particular the ease of producing a pharmaceutical composition according to the invention is enhanced through the use of L-cysteine or its precursor in a form substantially of a particle size which is less than 1,000 microns and conveniently less than the standard sieve size of 710 microns. By the phrase "substantially of a particle size" it is meant that a proportion by weight of at least 80 percent is of the size indicated, although preferably at least 90 percent and conveniently essentially 100 percent may be of the size indicated. The requirement as to a minimum particle size is less critical. However, conveniently less than 50 percent by weight and particularly less than 30 percent by weight of the L-cysteine or its precursor is of a particle size less than 250 microns.

It is preferred that a proportion of the L-cysteine or its precursor of at least 50% by weight, conveniently of at least 60% by weight and particularly of at least 70% by weight, is of a particle size in the range of 250 to 1,000 microns and conveniently of 250 to 710 microns.

It may be necessary to mill the commercially available sample of the L-cysteine-providing component of the composition to conform to the preferred particle size requirements indicated above. This is usually the case, for example, with DL-methionine but not with L-methionine. The size of the p-hydroxyacetanilide component of the mixture is of less significance and a commercially available sample may be suitable for direct use. Commonly, the particle size of such a sample may, for example, be such that a proportion of 50 to 60 percent by weight has a particle size of between 53 and 150 microns. If required, however, the material may be subjected to a simple screening procedure before use to ensure that it is substantially of a particle size less than a particular amount, for example 1,000 or particularly 710 microns. The phrase "substantially of a particle size" has the same meaning as previously and the same further preferences apply, i.e. preferably at least 90 percent by weight and conveniently essentially 100 percent by weight being of the size indicated.

In order to provide a pharmaceutical composition according to the invention which has an acceptable odour it is preferred that the amount of water in the composition is no more than 2.5 or 2.0 percent by weight of the whole, preferably no more than 1.5 or 1.0 percent and conveniently no more than 0.8 percent. Although the composition therefore preferably consists of essentially dry materials, the presence of some water is desirable for effective binding, so that the composition preferably includes an amount of water which is at least 0.4 percent by weight of the whole, preferably at least 0.5 percent and conveniently at least 0.6 percent.

The proportion by weight of water present in a pharmaceutical composition produced by the process of the present invention is thus preferably in a range from 0.4 or 0.5 to 2.5 percent by weight of the whole, with further preferences as to the upper and lower limits being as previously indicated, a particularly preferred range being from 0.5 to 1.0 percent, conveniently from 0.6 to 0.8 percent, for example 0.7 percent.

The amount of water present prior to the shaping of the composition will generally conform to the figures indicated for the composition as there is usually no significant change in water content involved in the process of shaping the mixture of compounds. The figures quoted for water content herein are those obtained by measurement using the Karl Fischer technique. This involves the use of a solution of iodine and sulphur dioxide in pyridine/methanol to titrate water. The reagent is commercially available.

As regards the L-cysteine-providing component of the pharmaceutical composition, either L-cysteine or any compound which is metabolised by the body to provide L-cysteine may be used. It will be appreciated that the compound need not necessarily all be converted to L-cysteine nor need all the L-cysteine be converted into glutathione. The function of this component is, in the event of an overdose of the drug being taken and the normal supply of glutathione in the body being exhausted, to provide a replacement source of L-cysteine.

In addition to L-cysteine itself, the naturally occurring amino acids of particular interest are L-cystine and particularly L-methionine, L-methionine being preferred to L-cysteine itself. The DL isomer of the sulphur-containing amino acids can also be used and in the case of methionine but not of cysteine both the D and L isomers provide a source of the L-cysteine component of glutathione. A D isomer may also contribute by the provision of intracellular sulphate. An L isomer and in particular L-methionine does have the advantage of greater purity and possibly of being available in a form having a particle size range which is acceptable for immediate use thereby avoiding the necessity of milling.

If desired, larger molecules such as di-, tri- or higher peptides which break down in vivo to give L-cysteine may be used, a particularly suitable type of dipeptide being one which provides two of the amino acid units of glutathione, i.e. L-glutamyl-L-cysteine or L-cysteinyl-glycine. Preferably however L-cysteine or another amino acid is used.

It will be appreciated that the L-cysteine-providing component may if desired be in the form of a salt with any physiologically acceptable acid or base. Thus, salts may be formed with various suitable inorganic and organic acids. Examples of such inorganic acids are phosphonic acid, nitric acid, sulphuric acid and particularly the hydrohalic acids hydrochloric acid, hydrobromic acid and hydroiodic acid. Examples of such organic acids are citric acid, oxalic acid, fumaric acid, maleic acid, lactic acid, succinic acid, malic acid, tartaric acid and methane sulphonic acid. Alternatively salts may be formed with various suitable inorganic and organic bases. Examples of these are the alkali metal hydroxides, for example sodium hydroxide, quaternary ammonium hydroxides and amines such as tris (tris representing 2-amino-2-hydroxymethyl propane 1,3-diol).

As regards the relative proportion of L-cysteine or its precursor and p-hydroxyacetanilide the major consideration is the provision of a sufficient supply of glutathione to counter toxicity in the event of an overdose of p-hydroxyacetanilide depleting the normal supply of glutathione. However, it is not desirable to include an unnecessarily large proportion of the L-glutathione providing compound. The proportion of this compound by weight relative to the p-hydroxyacetanilide will of course vary depending particularly upon the nature of the compound used but an amount in the range from 5 to 100%, conveniently 10 to 50%, and preferably 15 to 25%, for example 20%, is usually suitable.

In addition to p-hydroxyacetanilide and L-cysteine or its precursor, the composition may, if desired, contain other active ingredients, for example one or more of the compounds caffeine, caffeine hydrate, codeine, codeine phosphate, dihydrocodeine tartrate, pseudoephidrine hydrochloride and phenolphthaline. Of these compounds codeine and/or caffeine in one form of another are most usually formulated together with p-hydroxyacetanilide. It will be appreciated, however, that the present formulation will not counter any toxic effects arising from overdoses of these other ingredients. However, these effects may not be as severe as those arising from the p-hydroxyacetanilide and compositions additionally containing codeine or a salt thereof are of particular interest. In addition to its active ingredients a pharmaceutical composition produced according to the present invention will usually contain a physiologically acceptable solid carrier.

The present invention thus includes a shaped pharmaceutical composition comprising a non-granular solid mixture comprising p-hydroxyacetanilide and L-cysteine or a compound which is convertible thereto in vivo together with a physiologically acceptable solid carrier.

Moreover, the present invention further includes a pharmaceutical composition comprising a solid mixture of p-hydroxyacetanilide and L-cysteine or a compound which is converted thereto in vivo characterised in that the L-cysteine or its precursor is substantially of a particle size less than 1,000 microns.

A carrier material used in a pharmaceutical composition according to the present invention may be conventional to the art of pharmaceutical formulation but such materials are preferably selected in both nature and quantity with a view to producing particular physical properties for the composition. Thus, for example, the composition may conveniently contain one or more of a component which acts as a lubricant for flow of the various components together, a component which enhances adhesion of the components of the composition during shaping, and a component which aids dispersion of the composition in the body. Among these, the presence of an adhesive agent is of especial interst. Of particular value as a lubricant is a starch product such as sodium starch glycollate, for example Explotab; as an adhesive agent is a vinyl polymer, particularly an N-vinyl polymer such as polyvinylpyrrolidone, together with a cellulose product such as microcrystalline cellulose, for example Avicel PH102, which not only aids adhesion through conferring mechanical strength but which also exerts a wicking effect thereby aiding the action of the dispersing agent; and as a dispersing agent is magnesium stearate. These components may be present in conventional proportions, for example an amount by weight of the whole composition equal to 0.5 to 2 percent of sodium starch glycollate, for example 0.96 percent, 2 to 8 percent of polyvinylpyrrolidone, for example 4.08 percent, 0.15 to 0.6 percent of cellulose, for example 0.32 percent, and 0.7 to 3 percent of magnesium stearate, for example 1.44 percent, or a similar amount of an alternative to these materials performing a similar function.

The process of the present invention involves admixture of the various components, conveniently in an order commencing with the active ingredients followed by the carrier materials. However, the p-hydroxyacetanilide mixed with the L-cysteine or its precursor may conveniently be in a form in which it is already coated with the primary adhesive agent such as polyvinylpyrrolidone (p-hydroxyacetanilide being commercially available in such a coated form).

The advantage of using L-cysteine or its precursor in a physical form with a particular particle size has been discussed previously but the carrier materials, like the p-hydroxyacetanilide, may often be used in the physical form as supplied in the usual commercial samples of the material or alternatively may be subjected to a simple screening procedure to remove particles above 1,000 or particularly 710 microns. It will often be the case therefore that the whole mixture including the p-hydroxyacetanilide and the carrier materials conforms to the main preference indicated for the L-cysteine or its precursor so that it is substantially of a particle size which is less than 1,000 microns and conveniently less than 710 microns.

Following admixture, suitably using conventional techniques, the mixture is shaped or formed, particularly by compression using a suitable level of pressure. A conventional compression machine may be used and this will usually effect a degree of compression which produces a level of hardness in the range of about 5 to 12 kilopascals, for example 5 to 7 kilopascals. The shaped product will generally have the form of a tablet, conveniently with either an essentially circular cross section or an elliptical cross section with a length greater than its width. After shaping the product may be treated further as desired, for example to provide a coating which will assist in preventing the take up of moisture during storage. Such a coating may consist of wax or alternatively of a film forming polymer such as an acrylic polymer, for example the aminoalkyl methacrylate copolymer marketed under the trade name EUDRAGIT E100.

The compositions may conveniently be formulated in unit dosage form, i.e. in the form of discrete portions each containing a unit dose, or a multiple or sub-multiple of a unit dose, of p-hydroxyacetanilide.

The recommended daily dose of p-hydroxyacetanilide for an adult human patient is of the order of from about 1.5 to about 4 grams daily, as required, usually being divided into 3 or 4 spaced doses of from about 0.5 to about 1 gram and with the dose being approximately halved for children. Conveniently, therefore, individual tablets contain from 0.1 to about 2 grams, preferably from about 0.25 to about 0.75 or 1 gram and usually 0.5 grams. Veterinary doses are on a similar mg/kg basis but the present invention is of particular application to the production of pharmaceutical compositions for human use.

p-Hydroxyacetanilide is of value for use not only as an analgesic but also in other contexts, particularly as an antipyretic.

The present invention thus includes the use of a non-granular solid mixture comprising p-hydroxyacetanilide and L-cysteine or a compound which is converted thereto in vivo for the manufacture of a medicament for use as an analgesic or antipyretic.

Moreover, the present invention further includes the use of a solid mixture comprising p-hydroxyacetanilide and L-cysteine or a compound which is converted thereto in vivo in which the L-cysteine or its precursor is substantially of a particle size less than 1,000 microns for the manufacture of a medicament for use as an analgesic or antipyretic.

Also included by the present invention is a method for the treatment of a patient in need thereof, for example a patient requiring analgesic or antipyretic treatment, with a therapeutically effective amount of a pharmaceutical composition as described herein.

It will be appreciated that the present invention further includes any new process for the production of a pharmaceutical composition comprising p-hydrodyacetanilide and L-cysteine or a compound which is converted thereto in vivo, and also any such new a pharmaceutical composition, as is described hereinbefore.

The invention is illustrated by the following examples.

EXAMPLES

Example 1

Production of Composition of p-Hydroxyacetanilide and DL-Methionine

DL-Methionine was milled before use using either a Fitzmill or a dispersion mill in order to reduce the particle size of the commercial sample. Analysis of a typical milled sample shows the following distribution by weight on passing the material through a succession of standard sieves of decreasing size:

0.83% retained on 710 micron sieve;
63.6% retained on 300 micron sieve;
18.2% retained on 250 micron sieve;
10.76% retained on 150 micron sieve;
4.96% retained on 106 micron sieve, and
1.65% remaining.

p-Hydroxyacetanilide was treated with a solution of polyvinylpyrrolidone and dried in a fluid bed drier. (Such a coated material is commercially available.) The coated material was passed through a 710 micron sieve.

The DL-methionine (1556.49 g) was transferred into a 20 kg drum which had been cleaned and dried and the polyvinylpyrrolidone-treated p-hydroxyacetanilide (paracetamol, sieved D.C. grade, 95% p-hydroxyacetanilide and 5% polyvinylpyrrolidone by weight) (8171.60 g) was added to the drum. The drum was placed on an adapted Winkworth Turbula Blender and blending carried out for 10 minutes at 44 rpm.

Sodium starch glycollate (Explotab) (96.19 g) and microcrystalline cellulose (Avicel PH102) (31.59 g) were manually mixed in a clean double-lined polythene bag with approximately the same weight (127.78 g) of the blend of p-hydroxyacetanilide and methionine taken from the Blender. The mixture from the bag was then added to the remainder of the blend of p-hydroxyacetanilide and methionine in the Blender and the whole blended for 10 minutes at 44 rpm.

Magnesium stearate (158.54 g) was passed through a 710 micron mesh sieve and 144.13 g of the sieved material was added to a clean double-lined polythene bag. To the bag was then added approximately double the weight (288.26 g) of the blend of p-hydroxyacetanilide, methionine, sodium starch glycollate and microcrystalline cellulose from the Blender, the whole then being manually mixed in the bag for 3 minutes. The mixture from the bag was then added to the remainder of the blend of the other components in the Blender and the whole blended for 5 minutes at 44 rpm.

The bulk powder blend was transferred into double-lined polythene bags which were in turn placed, prior to tabletting, in lidded white polycarbonate pots laden with an ample supply of dessicant sachets. The powder was compressed into tablets in amounts of approximately 10,000 g using a Manesty-D3-B compression machine providing a hardness of 5 to 7 kilopascals. The target mass per tablet was 642.47 mg with the individual mass being within the ±5% target range of 611–674 mg. These tablets were placed in a coating pan which was then rotated. Beeswax (150 g) was dissolved in slightly warm industrial methylated spirit (IMS) (3 liters) at about 30° C. and 200 ml of the warm solution was sprayed from a spray container onto the rolling tablets in the coating pan. The tablets were allowed to polish for 5 to 10 minutes and were then packaged[1].

[1] In a variation of the coating procedure, coating was effected using talc and a solution of EUDRAGIT E100 in isopropanol/acetone.

In odour tests the tablets, although typically not completely odourless, possessed an odour much more acceptable to the human nose than the commercial product Pameton.

Example 2

Production of Composition of p-Hydroxyacetanilide and L-Methionine

The procedure of Example 1 was repeated exactly but replacing the 1556.49 g of DL-methionine by the same weight of L-methionine which did not, however, require milling before use.

I claim:

1. A process for the production of a pharmaceutical composition comprising p-hydroxyacetanilide and L-cysteine or a compound which is converted thereto in vivo which process comprises mixing p-hydroxyacetanilide and L-cysteine or its precursor in the solid state and then converting the solid mixture to a shaped product, wherein (i) the mixing and converting to a shaped product do not involve a wet granulation step, (ii) the L-cysteine or its precursor is substantially of a particle size less than 1,000 microns, and (iii) the shaping is by direct compression.

2. A process according to claim 1, in which the solid mixture is non-granular.

3. A process according to claim 1, in which the composition additionally comprises a physiologically acceptable solid carrier which is mixed with the p-hydroxyacetanilide and L-cysteine or its precursor in the solid state prior to shaping of the mixture.

4. A process according to claim 3, in which the carrier comprises the adhesive agent polyvinylpyrrolidone.

5. A process according to claim 1, in which the amount of water in the solid mixture is in the range of 0.5 to 2.5 percent by weight of the whole.

6. A process according to claim 1, in which p-hydroxyacetanilide and DL-methionine or a physiologically acceptable salt thereof are mixed in the solid state and then converted to a shaped product.

7. A process according to claim 1, in which p-hydroxyacetanilide and L-methionine or a physiologically acceptable salt thereof are mixed in the solid state and then converted to a shaped product.

* * * * *